United States Patent [19]

Kay

[11] Patent Number: 5,713,842
[45] Date of Patent: Feb. 3, 1998

[54] OCCLUSIVE WOUND DRESSING AND APPLICATOR WITH SAME FLEXIBILITY

[75] Inventor: Dennis Kay, Tampa, Fla.

[73] Assignee: Bioderm, Tampa, Fla.

[21] Appl. No.: 195,063

[22] Filed: Feb. 14, 1994

Related U.S. Application Data

[63] Continuation of Ser. No. 788,150, Nov. 6, 1991, abandoned.

[51] Int. Cl.⁶ .............................. A61F 13/00; A61F 15/00
[52] U.S. Cl. .................... 602/57; 602/58; 602/41; 206/444
[58] Field of Search .................... 602/41, 42, 52, 602/55, 57, 58; 604/307; 206/440, 441; 424/445

[56] References Cited

U.S. PATENT DOCUMENTS

| Re. 33,353 | 9/1990 | Heinecke . | |
|---|---|---|---|
| 4,310,509 | 1/1982 | Berglund et al. | 604/307 |
| 4,513,739 | 4/1985 | Johns | 602/57 |
| 4,600,001 | 7/1986 | Gilman | 602/57 |
| 4,699,792 | 10/1987 | Nick et al. | 604/307 |
| 4,904,247 | 2/1990 | Therriault et al. | 604/304 |
| 4,915,102 | 4/1990 | Kwiatek et al. | 602/57 |
| 4,917,112 | 4/1990 | Kalt | 604/307 |
| 4,928,680 | 5/1990 | Sandbank | 602/57 |

FOREIGN PATENT DOCUMENTS

| 91412/82 | 6/1983 | Australia . |
| 20254/83 | 5/1984 | Australia . |
| 20255/83 | 5/1984 | Australia . |
| 23832/84 | 8/1984 | Australia . |
| 22210/88 | 3/1989 | Australia . |
| 45750/89 | 6/1990 | Australia . |
| 0 161 865 | 11/1985 | European Pat. Off. . |
| 0 341 045 | 11/1989 | European Pat. Off. . |
| 0 409 587 | 1/1991 | European Pat. Off. . |
| 0 424 165 | 4/1991 | European Pat. Off. . |
| 0 434 258 | 6/1991 | European Pat. Off. . |
| WO 86/00220 | 1/1986 | WIPO . |

*Primary Examiner*—Paul B. Prebilic
*Attorney, Agent, or Firm*—Foley & Lardner

[57] ABSTRACT

A thin film wound dressing that is particularly easy to position accurately and apply smoothly to form an occlusive seal comprises three layers: a first wound covering layer being permeable to gases and water vapor while being impermeable to microbes and liquids; a second adhesive layer intimately disposed on the first layer for use in occlusively attaching the invention to skin or wound surfaces; and a third release backing layer disposed on the second adhesive layer. The release backing layer has a functionally contiguous or integral pull-tab attached in a manner that creates a substantially U-shaped release backing/pull-tab assembly. The release backing and pull-tab portions of the assembly are highly flexible while also being highly resistant to elongation to facilitate the smooth and wrinkle-free application of the first and second layers to skin or wound surfaces and formation of an occlusive, microbe and liquid impermeable barrier. The various layers of the invention are preferably transparent to light and may be impregnated or coated with antiseptics, antimicrobials or other medically active substances. The wound dressing is provided in non-polygonal shapes that eliminate redundant surface area and increase the effective adhesion to anatomic surfaces.

52 Claims, 6 Drawing Sheets

OCCLUSIVE WOUND DRESSING AND APPLICATOR WITH SAME FLEXIBILITY

This application is a continuation of application Ser. No. 07/788,150, filed Nov. 6, 1991 and now abandoned.

BACKGROUND OF THE INVENTION

The present invention relates to thin film wound dressings and, more particularly, to means and methodology for the application of such dressings to skin surfaces to provide a sterile mechanical barrier to all types of infectious agents.

Wound healing assistance and wound dressing technology have changed substantially in the last fifteen years due to a recognition of the fact that wound healing is aided by the provision of a more physiologic environment for the wound, especially with respect to gasses such as water vapor and carbon dioxide. The development of wound dressing technology has also been aided by recent advances in biocompatible synthetic materials, including thin films and adhesives that are permeable to gasses, including water vapor.

Improved wound care has been achieved via more effective wound dressings that are occlusive and protect the wound from the external environment.

More specifically, it has been shown that providing a sterile wound covering that is permeable to gasses including water vapor and impermeable to liquids and microbes is an aid to healing. Films of less than 3 mils in thickness are commonly employed in such dressings because thicker films are much less permeable to gas and water vapor. Several polyurethane films have been specifically adapted for wound dressings and other medical uses. These films are typically used in thicknesses of less than 2 mils and allow the free diffusion of oxygen, water vapor and other gasses through their molecular matrices. In addition, these films are impermeable to both liquids and to all known microbial disease vectors.

The use of vapor permeable membranes that remain effective as microbial barriers has been beset with problems because of the handling characteristics of thin films. A persistent problem in thin film dressing technology arises from an inherent cohesion between film surfaces. When such films are applied to wounds, wrinkles or tunnels result that can be infiltrated easily and quickly by disease vectors. The wrinkling associated with self-clinging characteristics is similar to the wrinkling that often occurs with plastic food wrap. This wrinkling completely eliminates the desired occlusive properties of a thin film wound dressing.

The problem of wrinkled dressing application is further exacerbated by the use of adhesives on thin film wound dressings. The adhesives on thin films increase cohesion and lead to the irreversible formation of wrinkles during application of the wound dressing. When wrinkles are formed in an adhesive-coated film during application to the skin or a wound surface, it is virtually impossible to achieve an occlusive seal. Absent such an occlusive seal, the functions of a wound dressing are markedly diminished.

Various approaches to solving this medical problem have evolved. Until the present invention, however, thin film wound dressings have had limited use as a medically effective wound dressing because of the difficulty in dependably achieving a wrinkle-free occlusive seal during application.

An example of a wound dressing which includes an applicator means designed to apply a thin film wound dressing in a wrinkle-free manner is shown in U.S. Pat. No. 4,915,102 (Kwiatek). The Kwiatek patent discloses a rectangular wound dressing interposed between a hinged, differentially releasing backing, so that the dressing can be applied after the front-hinged portion of the backing is unfolded and before the back-hinged portion is removed from the dressing. During application, the thin film dressing is adhered to the release backing member tenaciously enough that the dressing can be intimately applied to skin or wound surfaces without wrinkles. However, the stiffness of the back release member makes wrinkle-free application of this dressing to continuously curved anatomic surfaces difficult or impossible to achieve.

Once the Kwiatek dressing is applied, the back portion of the hinged-release layer must be removed from the wound dressing. This approach to applying a thin film dressing presents the disadvantage of requiring extra steps both in the application of the dressing to a wound and in dressing manufacture. Kwiatek's art also requires additional functional components, such as adhesives and release backing layers, having differing affinities for the various surfaces of the wound dressing.

Another approach to solving the problems inherent in thin film, gas-permeable wound dressings is shown in U.S. Pat. No. 4,917,112 (Kalt). Kalt discloses a transparent, gas-permeable thin film affixed to a semi-rigid surrounding frame that forms a window-like wound dressing. The dressing of Kalt however, comprises a rigid frame that lacks elasticity and is not easily conformed to the complex curves of anatomic surfaces. As a consequence, the rigid frame often does not form a uniformly, occlusive dressing-to-skin seal and is therefore not a preferred means for the application of thin film dressings to the complex curved contours of body surfaces.

Furthermore, U.S. Pat. No. 4,904,247 to Therriault, et al. discloses a pressure-sensitive, hydrophilic-layered, composite wound dressing but does not disclose a means for applying the dressing so that an occlusive seal is formed.

U.S. Pat. No. 4,600,001 to Gilman discloses a perforated wound dressing that is applied via a laminate release backing layer and a perforated removable backing layer. Gilman's backing layer is peripherally reinforced at opposite ends with tape tabs. After the backing layer and tape tabs are used to maintain the thin film layer in a relatively flat conformation during application, the backing layer is peeled away from the film surface. Portions of the film layer and the tape tabs must be separated at the perforations from the remaining film layer. Gilman does not facilitate an adequately occlusive application of a thin film dressing and is particularly inadequate for application to the complex curved body contours. Moreover, the dressing-to-skin seal may be disturbed at the time the tape tabs are removed. The stiff and flat nature of the upper release backing prevents the smooth and wrinkle-free application of the dressing to anatomic skin surfaces having curves. The additional upper release backing and tape tab components of Gilman require additional costly materials and manufacturing steps to produce a dressing which does not effectively solve the inherent problems of thin film wound dressings.

SUMMARY OF THE INVENTION

It is therefore an object of the present invention to provide a simplified means for handling a thin film in the context of applying the film as a wound dressing to a skin or wound surface.

It is also an object of the present invention to provide a method for the wrinkle-free placement and application of layered thin film wound dressings which are impregnated or treated with antiseptic, antimicrobial or other medically active substances.

It is another object of the invention to provide a wound dressing which is transparent to light, which is permeable to gasses and water vapor but impermeable to microbes and liquids, and which is readily applied to form an occlusive seal against skin and mucosal surfaces.

It is also an object of the present invention to provide wound dressings of diverse, non-polygonal shapes for optimal application and occlusive sealing to curved anatomic contours.

To satisfy these and other objects of the invention, a wound dressing is provided which has a first thin film layer that is impermeable to liquids and microbes but permeable to gasses and water vapor, and an adhesive second layer that is provided on the first layer, the adhesive layer also being permeable to gasses and water vapor, and a highly flexible release backing layer which resists elongation is provided on the adhesive second layer. In one embodiment of the invention, the highly flexible release backing layer is divided into at least two pieces and each of the pieces is provided with a pull-tab. The pull-tabs resist elongation such that application of opposing force sequentially to each of the pull-tabs, respectively, causes the removal of the release backing layer in a direction substantially transverse to the first layer so that the first and the second layers can be smoothly transferred to skin or wound surfaces to form a physical barrier that is microbe-impermeable.

In some embodiments of the invention the adhesive is disposed only on the periphery of the first layer. The first thin film layer can comprise one or more materials selected from the group consisting of polyurethane, polyethylene, acrylic and silicone.

The release backing layer comprises one or more materials selected from the group consisting of silicone coated paper, plastic film, plastic coated paper, low density polyethylene, metal foil and polypropylene. The pattern of the adhesive layer on the thin film layer defines a regular grid of adhesive material and a medically active substance is provided on the film layer in the interstices of the grid.

Within the scope of the invention are embodiments wherein only one release layer and one pull tab are provided. In those embodiments, a wound dressing comprises a first thin film layer that is impermeable to liquids and microbes but permeable to gasses and water vapor the first layer having a bonding surface and an external surface with an adhesive second layer that is provided on the bonding surface of the first layer. The adhesive layer is also permeable to gasses and water vapor while being impermeable to liquids and microbes.

A highly flexible release backing layer which resists elongation is provided on the adhesive second layer, and a pull-tab is provided on the release backing layer wherein the pull-tab also resists elongation such that application of force to the pull-tab, in a direction away from and substantially parallel to the first and second layers, causes the removal of the release backing layer in a direction substantially transverse to the first layer so that the first and second layers can be smoothly transferred to skin or wound surfaces to form a physical barrier that is microbe-impermeable. An affixation tab is disposed on the external surface of the first layer for affixing the dressing to a skin surface and for opposing the force to the pull tab as the release backing is being removed and the first and second layers are being applied to the skin surface.

In accordance with other objects of the invention, a method of treating a wound with the dressing of the invention is also provided. The method comprises the steps of: orienting, with respect to a wound site, a transparent, thin film wound dressing, which comprises a first thin film layer that is impermeable to liquids and microbes but permeable to gasses and water vapor, an adhesive second layer that is provided on the first layer, the adhesive layer also being permeable to gasses and water vapor, and a highly flexible release backing layer provided on the adhesive second layer, wherein the release backing layer is divided into at least two pieces and each of the pieces is provided with a pull-tab and the pull-tabs resist elongation such that application of force in a direction away from and substantially parallel to the first and second layers, causes the removal of the release backing layer in a direction substantially transverse to the first layer so that the first and the second layers can be sterilely transferred to skin or wound surfaces to form a physical barrier that is microbe-impermeable. Secondly, the method comprises sequentially removing the release backing layer pieces so that the dressing does not form wrinkles and occlusively contacts the skin or wound surface around the wound site, and simultaneously applying smoothing pressure to the dressing while removing the release backing layers so that a microbe-impermeable seal is achieved.

In accordance with yet other objects of the invention, thin film materials are provided which are suitable for use as release backing materials for medical devices wherein the materials are highly flexible yet highly resistant to elongation.

In a preferred embodiment of the invention, the adhesive second layer is disposed only on the periphery of the first layer. The first thin film layer of the invention is made of one or more materials selected from the group consisting of polyurethane, polyethylene, acrylic and silicone with a preferred material being polyurethane. The thin film layer is preferably 0.4 to 2.0 mils thick.

In one preferred embodiment of the invention, the pull-tabs extend to the periphery of the first and second layers and in other preferred embodiments, the pull-tabs extend to lie within the periphery of the first and second layers, or extend beyond the periphery of the first and second layers. The adhesive of the second layer is a medical grade acrylic adhesive compound and the release backing layer is made of one or more materials selected from the group consisting of silicone coated paper, plastic film, plastic coated paper, low density polyethylene, metal foil and polypropylene. A preferred material is polyethylene film.

Still in accordance with other objects of the invention, the first and second layers are transparent to light. Also, the release backing layer is divided into two portions along an approximately transverse midline perpendicular to the long axis of the device and can abut or overlap at such a line.

In accordance with further objects of the invention, the adhesive layer is impregnated with an antiseptic substance such as povidone iodine or an antimicrobial substance such as Neosporin (polymyxin B sulfate-bacitracin zinc-neomycin sulfate antibiotic). The adhesive layer can also be provided either continuously or discontinuously in a pattern and the interstices of the discontinuous pattern can be filled with antimicrobial or antiseptic substances. The dressings of the invention can also be provided with substances which further aid healing such as epidermal growth factor.

In accordance with other objects, the invention is provided in various shapes having no corners to conform to fit anatomical surfaces and to decrease the detaching forces which tend to become concentrated in the corners of conventional wound dressings.

Other objects, features and advantages of the present invention will become apparent from the following detailed description. It should be understood, however, that the detailed description and the specific examples, while indicating preferred embodiments of the invention, are given by way of illustration only. The detailed description herein will suggest changes and modifications within the spirit and scope of the invention that may become apparent to those skilled in the art. These changes and modifications are considered within the scope of the subject invention.

DETAILED DESCRIPTION OF THE PREFERRED EMBODIMENTS

The present invention is a wound dressing which is a laminate of a thin film, an adhesive, and a release backing/pull-tab assembly. By combining the functions of a backing or support layer with those of a release backing/pull-tab assembly, the present invention solves the problems inherent in applying and occlusively sealing thin film wound dressings. More specifically, the present invention combines a highly flexible and highly elongatable layer of thin film having a medically acceptable adhesive thereon with a release backing/pull tab layer which is both highly flexible and resistant to elongation. The highly flexible release backing layer preferably has substantially the same flexibility as the highly flexible thin layer. These three layers interact so that the separation of the layers from one another results in the wrinkle-free application of the thin film layer to a wound site.

The thin film layer can be applied to form an occlusive seal because the differences in the elongation characteristics of the thin film layer and the release backing/pull-tab layer focus the forces applied through the pull tabs to create a straight front line of separation at the area of contact of the release backing layer and the adhesive layer.

The pull-tabs possess a sufficiently high resistance to elongation that the force transmitted through the pull tab is focused on the release layer at a straight line of separation of the release layer from the adhesive layer. This line of separation is wrinkle-free and straight. The great flexibility of the release backing layer and its resistance to elongation are essential characteristics of the invention. The pull tab and release backing materials are both highly flexible and have high resistance to elongation so that the force applied to the pull tab is directly transmitted to a straight moving front line of separation between the release backing and the adhesive layer on the thin film as the release backing is pulled away from the thin film and adhesive layers. Because the interaction between the highly flexible and highly stretchable thin film layer having an adhesive thereon and the highly flexible release backing layer which is resistant to elongation results in a straight and wrinkle-free line of separation, the application of opposing forces to the pull tabs, respectively, causes a smooth transverse removal of the release backing layer pieces so that the first and second layers can be smoothly transferred to skin or wound surfaces to form a physical barrier that is microbe impermeable.

The straight and wrinkle free rolling front line of separation phenomenon appears to occur because of or simultaneously with the lack of perpendicular torque forces on the thin film layer at the rolling front of separation. In a conventional wound dressing using pull tabs, torque forces created during removal of a release backing cause that portion of the dressing which is not yet applied to rotate away from the application surface at the line of separation. This "stand-up" of the unapplied dressing layer permits or causes a curved or crooked rolling front of separation to form which in turn results in a wrinkled or non-occlusive application. In the present invention, however, torque forces which would raise that portion of the thin film dressing to be perpendicular to the application surface during removal of the release backings are not present.

Thus, in the present invention, force applied to a pull tab is distributed such that it removes the release layer while the first and second layers remain folded over to lie substantially parallel to that portion of the release backing layer which has already separated from the first and second layers. Alternatively stated, the force applied to a pull tab is transmitted to the first and second layers without causing them to rotate away from the release backing layer. As a result, when traction is applied to a pull tab, a straight rolling front line of separation is created as the release backing layer is removed and the portion of the thin film layer which is not yet applied to the skin surface remains parallel to that surface. Thus, the present invention has successfully coupled the force transmission characteristics of a highly flexible yet non-elongatable release backing with the highly flexible and highly stretchable characteristics of thin films to produce a wound dressing which solves the application problems inherent in the application of thin films.

A wound dressing of the present invention has a first layer that is impermeable to liquids and microbes but permeable to gasses and water vapor. An adhesive second layer, on the order of 1 mil in thickness, is provided on the first layer.

The adhesive layer is also permeable to gasses and water vapor. The third layer is a release backing layer provided on the adhesive second layer. The release backing layer is typically provided in thicknesses of less than 8.0 mils. In one embodiment of the invention, the release backing layer is divided into at least two pieces and each of the pieces is provided with a pull-tab. In another embodiment of the invention, the thin film layer is provided with an affixation tab for placing and holding one peripheral portion of the device to an anatomic surface, and a pull-tab near an opposite peripheral portion which pull-tab is contiguous with the release backing layer.

While not essential, the adhesive second layer may be disposed only on the periphery of the film layer. Adhesives suitable for this purpose include acrylic medical skin adhesives that possess controllable affinities for skin surfaces, and the synthetic films suitable for use in the invention. Of course, other adhesives known in the art which are compatible with both skin and the materials of the invention are also suitable.

The pull-tabs employed in the present invention can be of various lengths and, in one preferred embodiment, can extend beyond the periphery of the first and second layers to provide a longer handle end that further facilitates the ease of application. For reasons of simplicity of use and ease of manufacture, the pull-tabs and release backing layer can be contiguously formed of the same material which is highly resistant to elongation. In such a preferred embodiment, the material is folded back on itself to form a release backing/pull-tab assembly.

With respect to the release backing and pull tab components of the invention, "U-shaped" means that the pull tab component of the release backing/pull tab assembly is substantially parallel to the corresponding release backing component and the two are connected at their respective ends by an adhesive or by a weld so that the pull tab and the release backing approximate the arms of the letter "U" with the bottom of the "U" being the juncture of the two pieces. This juncture is of relatively small dimension when compared to the lengths of the pull tab and backing so that the arms of the "U" are relatively long. Alternatively, the pull tab and release backing portions can be of one piece folded back on itself to also form, substantially, a "U" shape with the fold therein being the bottom of the "U".

The pull tabs can be of various lengths, for example, in one preferred embodiment, the pull tab portion of the backing is longer than the release portion. In other preferred embodiments, the pull tab portion of the backing extends only far enough to lie within the periphery of the first layer or extends precisely to the periphery of the dressing. The conformability of the thin film and the design of the release backing/pull tab assemblies facilitates a smooth, wrinkle-free application of the film to an anatomic surface.

It is also preferable that both the first film layer and second adhesive layer are transparent to light, to thereby facilitate the placement and positioning of the subject dressing relative to a wound. Optionally, the release backing layer may also be of transparent material, to further facilitate the accurate application of the subject dressing. High transparency is an additional characteristic which makes polyurethane films preferred materials.

Either the first film layer or the second adhesive layer or both layers can be impregnated or coated with antiseptic, antimicrobial or other medically active substances or combinations thereof. Preferred antiseptic agents include povidone iodine and benzalkonium chloride. Preferred medically active substances include, but are not limited to, growth factors, clotting factors and other pharmaceutically and/or physiologically active compounds. In one preferred embodiment, the adhesive is combined with an antimicrobial such as Neosporin (polymyxin B sulfate-bacitracin zinc-neomycin sulfate antibiotic) or bacitracin and a growth factor such as Epidermal Growth Factor or Human Growth Hormone when the adhesive layer is applied during manufacture.

Various adhesives, antiseptics, antimicrobials and other medically active substances can also be applied to the film in various patterns, such as grids. Thus, an additional embodiment of the present invention provides a grid pattern of adhesive and has the grid interstices filled with antimicrobial or antiseptic compounds. This grid loading embodiment facilitates the use of antimicrobial, antiseptic or other medically active substances that are not compatible when mixed directly with a particular adhesive. A speckled overspray, either on the thin film layer or on the adhesive layer, is an alternative means of applying substances which do not mix well with the employed adhesive or are incompatible therewith.

Conventional wound dressings typically have corners. Once applied to an anatomic surface, the stresses on the thin film layer become concentrated in the corners. Increased stress and changes in body contour associated with movement often result in failure of the occlusive seal in an unacceptably short period of time. Dressings of the present invention are provided in shapes without corners (i.e. without discontinuous intersections of the film edges) and without other redundant surface areas. The shapes of the subject invention substantially increase the opportunity for occlusive dressing application and the effective life of the occlusive seal. Ellipsoid or circular shapes are particularly advantageous for application to complex curved body contours. Additional embodiments include any shape with a continuous curvature or a combination of curved and straight lines so that the dressing contour facilitates lasting occlusive dressing application.

With respect to the film layer, polyurethane films are preferred because of their light transparency, permeability to gasses and water vapor and impermeability to liquids and microbes. The transparency of polyurethane films allows the advantage of close observation of the progress of wound healing without the removal of the dressing. Other materials with similar characteristics may also be employed.

A preferred embodiment of the subject invention can be manufactured using polyurethane film in a thickness range from 0.5 mils to 2.0 mils. Other films of various thicknesses and composition may be used to practice the invention, provided that the characteristics of transparency, permeability to gasses and water vapor and impermeability to liquids and microbes are maintained. The release backing and pull tab assembly of the present invention is easily adaptable to use with other medical devices requiring release backings and/or pull tabs for the protection and subsequent application of an adhesive surface of a medical device to a body surface or object.

Figure 1:
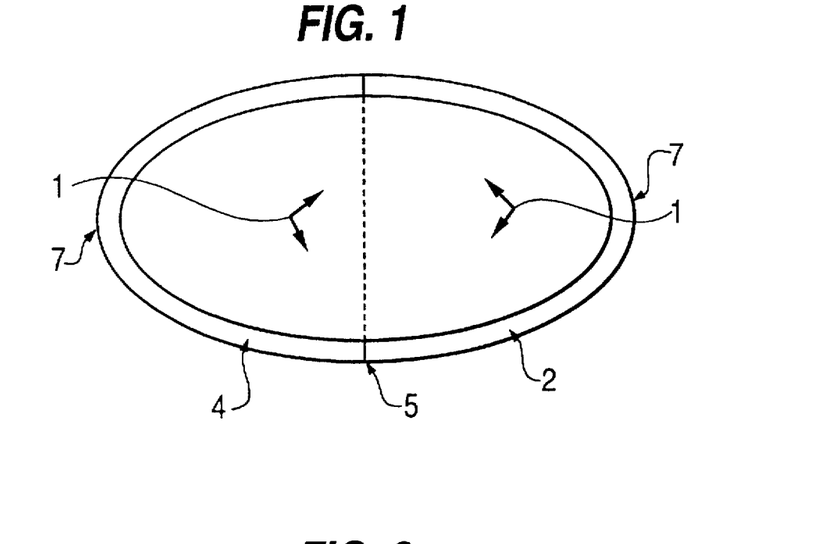
FIG. 1 is a plan view of an elliptical-shaped, thin film wound dressing of the present invention.

The wound dressing illustrated in FIG. 1 comprises a thin film continuous polyurethane layer 1 having a second adhesive layer (not shown) interposed between the polyurethane film layer and the two release backing/pull tab assemblies 2 and 4. The release backing/pull tab assemblies 2 and 4 abut at juncture line 5 (shown as a dotted line beneath the level of layer 1) and are provided with pull tab ends 7 for grasping and applying the invention.

Figure 2:
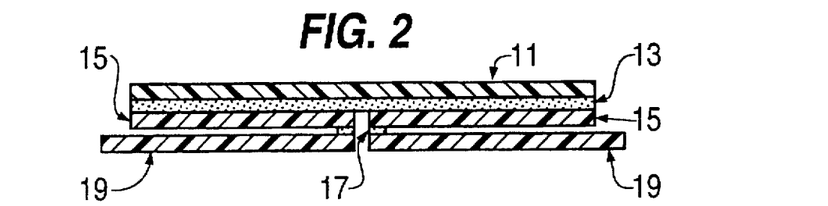
FIG. 2 is a cross-sectional view of the wound dressing, which view is perpendicular to the view of FIG. 1, illustrating various layers and a junction between release backing layers and pull-tabs.

FIG. 2 illustrates the various components of the present invention in exaggerated thickness dimension for clarity of the relationships shown. Specifically, polyurethane film layer 11 typically has a thickness on the order of 1.0 mil and has adhesive layer 13 applied thereto. Adhesive layer 13 is interposed between polyurethane film layer 11 and release backing 15. In this embodiment, each portion of release backing 15 is attached to a pull-tab 19 via a plastic weld at juncture 17. Juncture 17 is located at an analogous position to juncture line 5 of FIG. 1. While a gap between release backing layers 15 at juncture 17 is shown in exaggerated manner for the purposes of illustration, in the practice of the invention, no gap exists at juncture 17 near the center of the wound dressing. In other embodiments of the invention, the release backing/pull tab assemblies overlap where they meet at the approximate center of the dressing.

Juncture 17 crosses the shorter axis of the dressing substantially perpendicular to and generally centered on the long axis of the dressing.

Figure 3:
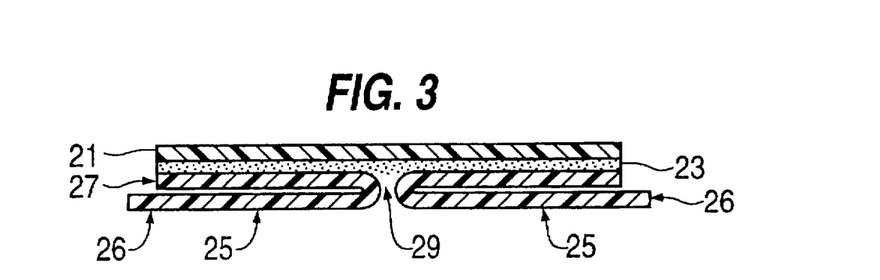
FIG. 3 is a similar cross-sectional view of an embodiment of the present invention wherein the pull-tab and release backing layer are continuous.

FIG. 3 illustrates, in an exaggerated fashion, the various components of another embodiment of the present invention. Polyurethane film layer 21, also of a thickness on the order of 1 mil, is provided with adhesive layer 23 and release backing layers 27 which are contiguous with pull-tabs 25. Taken together, each backing 27 and the contiguous pull-tab 25 form a release backing/pull-tab assembly. Each pull-tab 25 has a handle end 26 located at a point most distant from the U-shaped junction with the contiguous release backing 27. The two U-shaped release backing/pull-tab assemblies abut at line 29.

Figure 4:
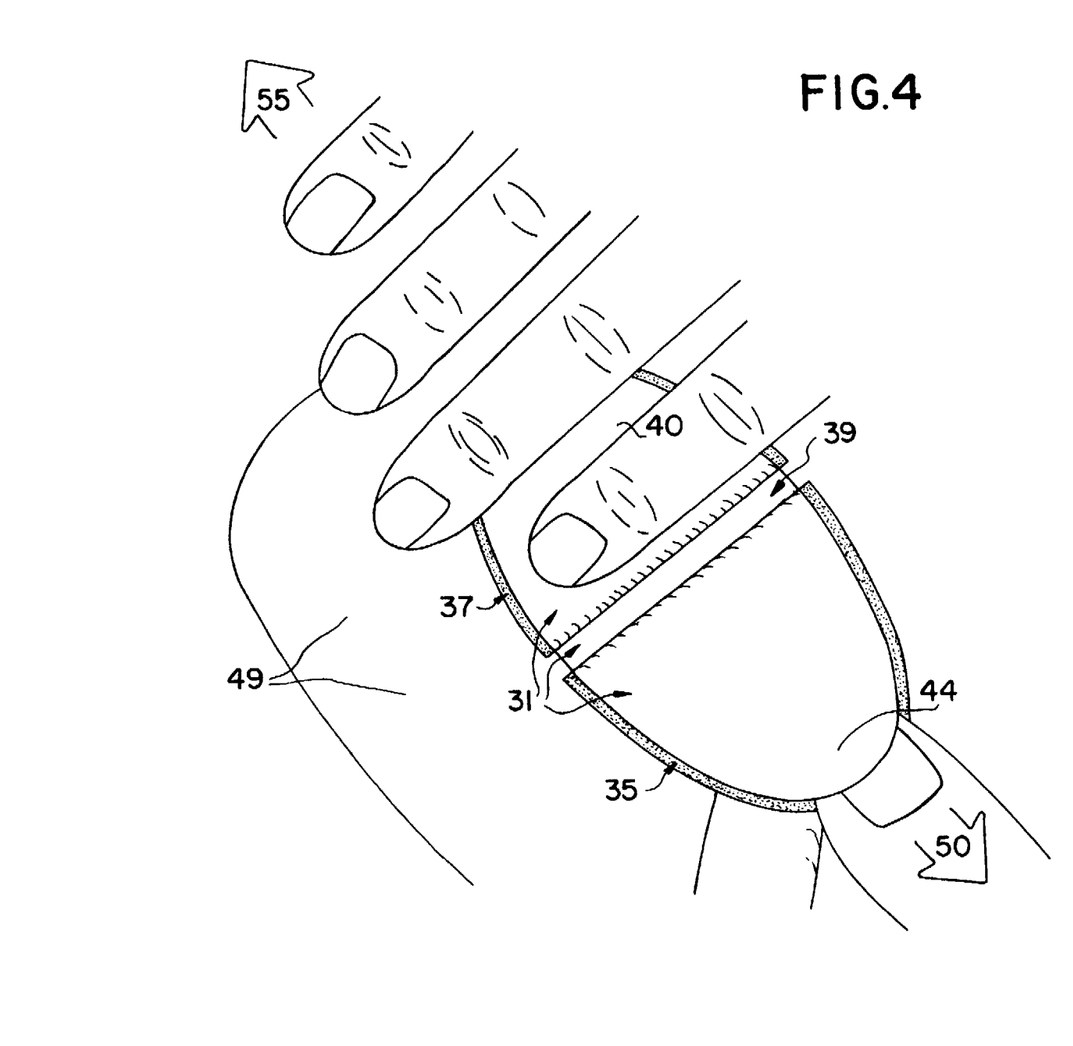
FIGS. 4, 5 and 6 depict, respectively, initial, intermediate and later stages of applying a wound dressing of the invention to a skin surface.
Figure 5:
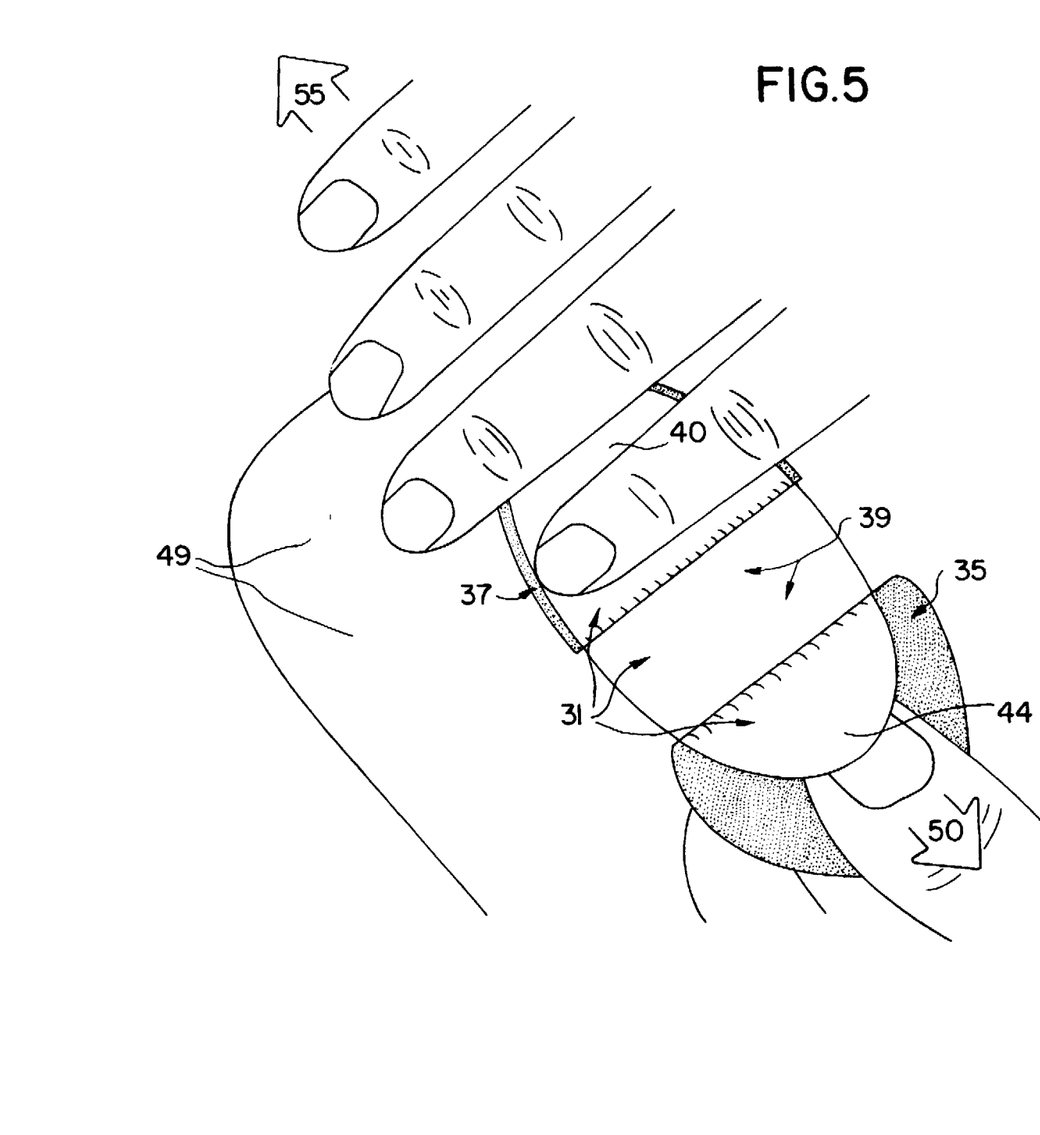
Figure 6:
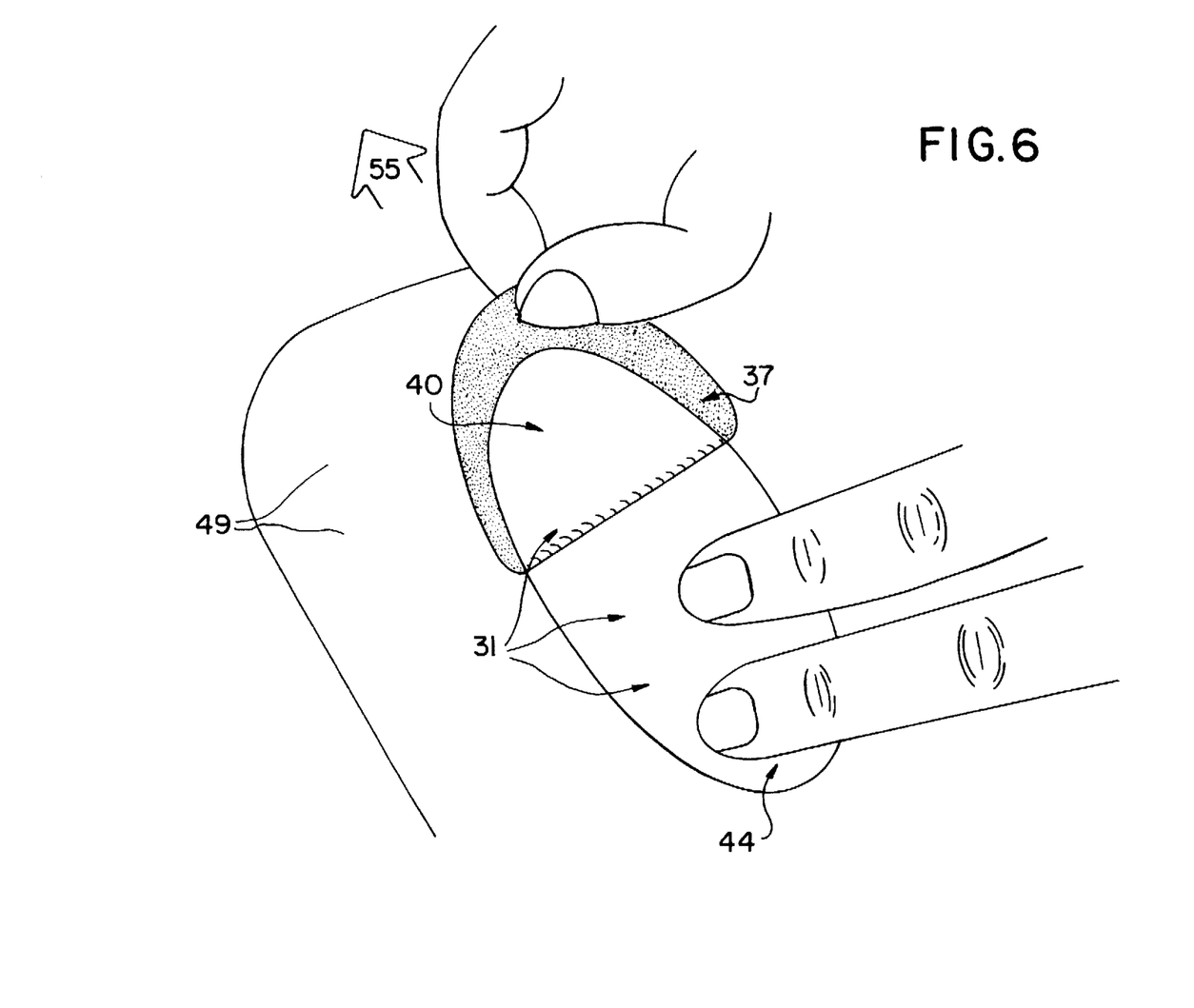

FIGS. 4, 5 and 6 depict the operation of a preferred embodiment of the present invention, wherein the release backing layer and pull-tabs are contiguous.

With reference to FIG. 4, the wound dressing of the subject invention is applied to anatomic surface 49 in the following manner: end 40 of the wound dressing is stabilized with respect to opposite end 44 by grasping end 40 or by pinning end 40 against the anatomic surface, as shown. Sufficient force is then applied by grasping the handle end of the pull-tab portion of pull-tab and release backing layer assembly 35 and pulling the handle end in the direction of arrow 50 to cause the partial removal of the release backing portion of the pull-tab and release backing layer assembly 35 from polyurethane film layer and adhesive layer assembly 31. This action forms a gap 39 between release backing/pull-tab assembly 35 and release backing/pull-tab assembly 37. Since film layer 31 is transparent, gap 39 facilitates observation of the central portion of the wound and accurate application of the central portion of the dressing to the central portion of the wound.

With reference to FIG. 5, continued traction is applied to assembly 35 in the direction of arrow 50. Gap 39 widens further and polyurethane film and adhesive layer assembly 31 intimately contact anatomic surface 49. Continued force in the direction of arrow 50 causes release backing/pull-tab assembly 35 to come completely away from film/adhesive assembly 31 resulting in intimate adhesion of assembly 31 to skin surface 39 over the entire area of assembly 31 that was formerly protected by assembly 35.

In FIG. 6, the final steps to apply the subject wound dressing are performed. Traction is applied to the handle end of the pull-tab portion of the release backing/pull-tab assembly 37 in the direction of arrow 55 until end 40 of thin film/adhesive assembly 31 is completely released from release backing/pull-tab assembly 37. As backing assembly 37 is completely removed from film assembly 31, film assembly 31 achieves complete and intimate contact with anatomic surface 49. Provided that assembly 31 is smoothed into place on surface 49 with fingers, during the application process described above, a smooth and wrinkle free application of the subject dressing can be achieved.

Figure 7:
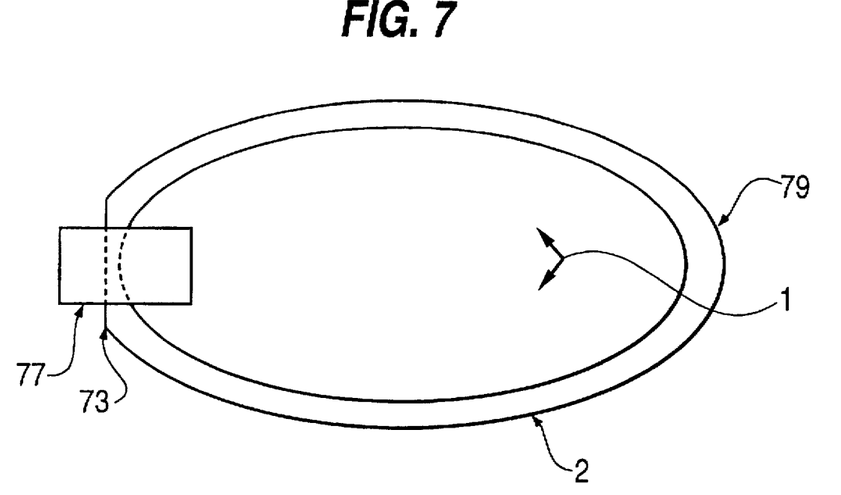
FIG. 7 is a plan view of an embodiment of the present invention having one affixation tab and one pull-tab disposed opposite to one another.
Figure 8:
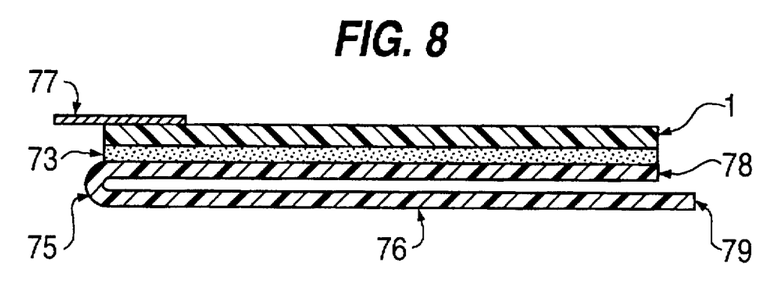
FIG. 8 depicts a cross-sectional view of the embodiment shown in FIG. 7, which view is perpendicular to that of FIG. 7, illustrating the relationships between the various layers and tabs.
Figure 9:
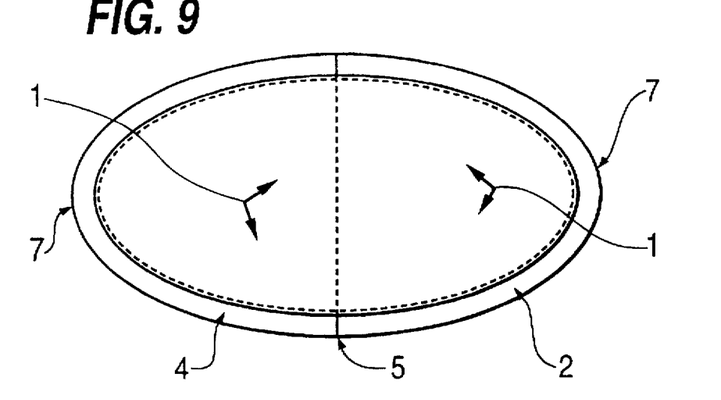
FIG. 9 is a plan view showing the adhesive layer (represented by dashed lines) on the periphery of the thin film layer.
Figure 10:
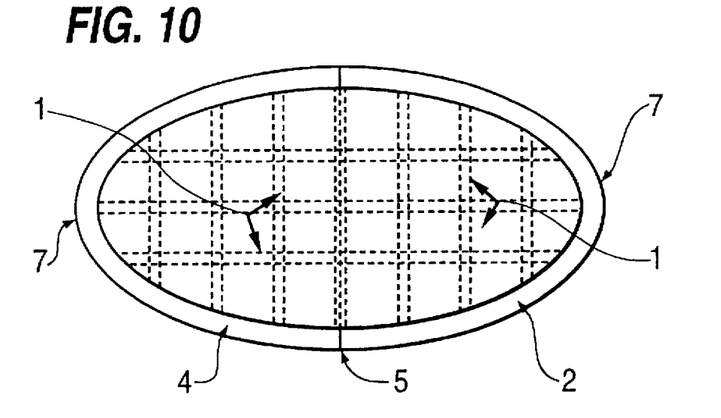
FIG. 10 is a plan view showing a discontinuous adhesive layer (represented by dashed lines) in a grid pattern.
Figure 11:
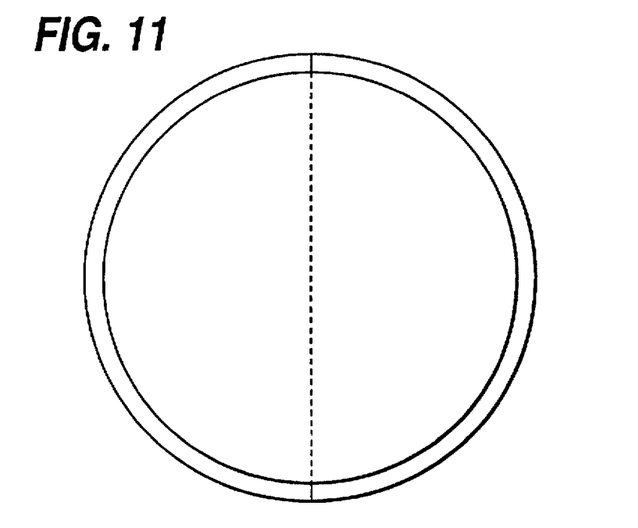
FIG. 11 is a plan view showing a substantially circular wound dressing.

With respect to FIGS. 7 and 8, an alternative embodiment of the invention having only one release backing/pull tab assembly and one affixation tab is shown. In both illustrations, the adhesive layer is interposed between the film and release backing layer but is not shown.

With reference to the embodiment of the invention shown in FIGS. 7 and 8, continuous polyurethane layer 1 is provided with affixation tab 77 on its exterior surface and with adhesive layer 73 on its interior surface. Release backing portion 78 of the release backing/pull tab assembly is provided on adhesive layer 73 and is contiguous with pull tab portion 76 at fold 75. Pull tab portion 76 is provided with handle portion 79 at the end most distal to affixation tab 77.

The embodiment of the invention shown in FIGS. 7 and 8 operates in much the same manner as the embodiments shown in FIGS. 1–6 with affixation tab 77 functioning as a grasping point for applying an opposing force to the force applied to pull tab handle portion 79 of the single release backing/pull tab assembly.

From the foregoing description, it is evident that there are a number of changes, adaptations and modifications of the subject invention that are within the province of those persons having ordinary skill in the pertinent art. The inventor intends that all such variations, not departing from the spirit of the subject invention, be considered as within the scope of the subject invention as limited only by the appended claims.

What is claimed is:

1. A wound dressing comprising:

a highly flexible thin film layer having a transverse axis;

an adhesive layer provided on said flexible thin film layer; and a highly flexible release backing film layer releasably attached directly to said adhesive layer, said release backing layer being divided into at least two backing pieces, said backing pieces having substantially the same flexibility as said flexible thin film layer and attached directly to said adhesive layer, a first of said backing pieces releasably attached to said adhesive layer on one side of said transverse axis of said flexible thin film layer and a second of said backing pieces releasably attached to said adhesive layer on another side of said transverse axis of said flexible thin film layer, each of said backing pieces having a pull-tab attached thereto, each said pull-tab flexible film material having substantially the same flexibility as said flexible thin film layer, each said pull-tab extending away from said transverse axis of said flexible thin film layer.

2. A wound dressing comprising:

a highly flexible thin film layer having a bonding surface and an external surface;

an adhesive layer provided on said bonding surface of said flexible thin film layer;

a highly flexible release backing film layer releasably attached directly to said adhesive layer, said release backing layer having a single backing piece and a pull-tab, said single backing piece and said pull-tab having substantially the same flexibility as said flexible thin film layer, said single backing piece being releasably attached to said adhesive layer, said pull-tab being attached to one end of said backing piece; and an affixation tab disposed on said external surface of said flexible thin film layer.

3. A wound dressing comprising:

a flexible thin film layer;

an adhesive layer provided on said flexible thin film layer; and a highly flexible release backing film layer releasably attached directly to said adhesive layer, and having substantially the same flexibility as said flexible thin film layer, said flexible release backing layer having at least one backing piece releasably attached to said adhesive layer and a pull-tab attached to said at least one backing piece.

4. A wound dressing comprising:
a highly flexible thin film layer;
an adhesive layer provided on said flexible thin film layer; and
a highly flexible release backing film layer releasably attached directly to said adhesive layer, and having substantially the same flexibility as said flexible thin film layer.

5. A wound dressing consisting essentially of:
a highly flexible thin film layer;
an adhesive layer provided on said flexible thin film layer; and
a highly flexible release backing film layer releasably attached directly to said adhesive layer and having substantially the same flexibility as said flexible thin film layer.

6. A wound dressing comprising:
a highly flexible thin film layer made of polyurethane;
an adhesive layer provided on said flexible thin film layer; and
a highly flexible release backing layer releasably attached directly to said adhesive layer, said flexible release backing layer made of polyurethane and having substantially the same flexibility as said flexible thin film layer.

7. A wound dressing as defined in claim 1, wherein said adhesive layer is disposed only on a periphery of said flexible thin film layer.

8. A wound dressing as defined in claim 1, wherein said flexible thin film layer comprises one or more materials selected from the group consisting of polyurethane, polyethylene, and silicone.

9. A wound dressing as defined in claim 1, wherein said flexible thin film layer comprises polyurethane.

10. A wound dressing as defined in claim 1, wherein said flexible thin film layer is from 0.5 to 2.0 mils thick.

11. A wound dressing as defined in claim 1, wherein said flexible thin film layer is from 0.4 to 0.6 mils thick.

12. A wound dressing as defined in claim 1, wherein said flexible thin film layer is from 0.6 to 1.1 mils thick.

13. A wound dressing as defined in claim 1, wherein said adhesive layer comprises a medical grade acrylic adhesive compound.

14. A wound dressing as defined in claim 1, wherein said flexible thin film layer and said adhesive layer are transparent to light.

15. A wound dressing as defined in claim 14 wherein said backing pieces and each said pull-tab are transparent to light.

16. A wound dressing as defined in claim 1 wherein said adhesive layer is impregnated with an antiseptic.

17. A wound dressing as defined in claim 16, wherein said antiseptic comprises povidone iodine.

18. A wound dressing as defined in claim 1 wherein said adhesive layer is impregnated with an antimicrobial substance.

19. A wound dressing as defined in claim 18 wherein said antimicrobial substance comprises polymyxin B sulfate-bacitracin zinc-neomycin sulfate antibiotic.

20. A wound dressing as defined in claim 1 wherein said adhesive layer is provided discontinuously in a pattern.

21. A wound dressing as defined in claim 1 wherein said adhesive layer is provided continuously.

22. A wound dressing as defined in claim 20, wherein (i) said pattern defines a regular grid of adhesive material and (ii) a medically active substance is provided on said flexible thin film layer in the interstices of said grid.

23. A wound dressing as defined in claim 22, wherein said medically active substance comprises one or more substances selected from the group consisting of antimicrobials and antiseptics.

24. A wound dressing as defined in claim 22 wherein said medically active substance comprises one or more substances selected from the group consisting of povidone iodine and polymyxin B sulfate-bacitracin zinc-neomycin sulfate antibiotic.

25. A wound dressing as defined in claim 22 wherein said medically active substance improves healing.

26. A wound dressing as defined in claim 22 wherein said medically active substance is epidermal growth factor.

27. A wound dressing as defined in claim 1 wherein a perimeter of said wound dressing is shaped to fit anatomical surfaces.

28. A wound dressing as defined in claim 27, wherein said perimeter of said wound dressing has an absence of corners.

29. A wound dressing as defined in claim 27 wherein said wound dressing is substantially elliptical in shape.

30. A wound dressing as defined in claim 27 wherein said wound dressing is substantially circular in shape.

31. A wound dressing as defined in claim 1, wherein each of said backing pieces is continuous with its said pull-tab.

32. A wound dressing as defined in claim 2 wherein said affixation tab is removable.

33. A wound dressing as defined in claim 2, wherein said single backing piece and said pull-tab are contiguous.

34. A wound dressing as defined in claim 1, wherein each said pull-tab extends beyond a periphery of said flexible thin film layer.

35. A wound dressing as defined in claim 1, wherein said transverse axis lies across a center of said flexible thin film layer.

36. A wound dressing as defined in claim 1, wherein:
said flexible thin film layer comprises a material impermeable to liquids and microbes but permeable to gasses and water vapor;
said adhesive layer comprises a material permeable to gasses and water vapor; and
said backing pieces and each said pull-tab are resistant to elongation so that, when force is applied to said pull-tab to detach an associated one of said backing pieces from said adhesive layer, said associated one of said backing pieces detaches along a line of separation substantially transverse to said flexible thin film layer to apply said flexible thin film layer to one of a skin and a wound surface to form a wrinkle-free, microbe-impermeable, physical barrier.

37. A wound dressing as defined in claim 2, wherein:
said flexible thin film layer comprises a material impermeable to liquids and microbes but permeable to gasses and water vapor;
said adhesive layer comprises a material permeable to gasses and water vapor; and
said backing piece and said pull-tab are resistant to elongation so that application of force to said pull-tab detaches said backing piece from said adhesive layer along a line of separation substantially transverse to said flexible thin film layer to apply said flexible thin film layer to one of a skin and a wound surface to form a wrinkle-free, microbe-impermeable, physical barrier.

38. A wound dressing as defined in claim 1, wherein said flexible thin film layer comprises polyurethane and said flexible release backing layer comprises at least one film material that (A) has substantially the same flexibility as said polyurethane of said flexible thin film layer and (B) is selected from the group consisting of polyurethane, low density polyethylene, polypropylene, polybutylene, and silicone.

39. A wound dressing as defined in claim 1, wherein said flexible thin film layer and said flexible release backing layer both comprise a polyurethane film material.

40. A wound dressing as defined in claim 1, wherein said adhesive layer has uniform adhesive strength between said flexible thin film layer and said flexible release backing layer.

41. A wound dressing as defined in claim 1, wherein each of said backing pieces and its said pull-tab are substantially parallel.

42. A wound dressing as defined in claim 2, wherein said flexible thin film layer comprises polyurethane and said flexible release backing layer comprises one or more film materials having substantially the same flexibility as said polyurethane of said flexible thin film layer, said one or more film materials selected from the group consisting of polyurethane, low density polyethylene, polypropylene, polybutylene, and silicone.

43. A wound dressing as defined in claim 2, wherein said flexible thin film layer and said flexible release backing layer comprise a polyurethane film material.

44. A wound dressing as defined in claim 2, wherein said adhesive layer has uniform adhesive strength between said flexible thin film layer and said flexible release backing layer.

45. A wound dressing as defined in claim 2, wherein said single backing piece and said pull-tab are substantially parallel.

46. A wound dressing as defined in claim 2, wherein said single backing piece has a surface area greater than a surface area of said flexible thin film layer.

47. A wound dressing as defined in claim 2, wherein said pull-tab has a length greater than a length of said flexible thin film layer.

48. A wound dressing as defined in claim 3, wherein said flexible thin film layer comprises polyurethane and said flexible release backing layer comprises one or more film materials having substantially the same flexibility as said polyurethane of said flexible thin film layer, said one or more film materials selected from the group consisting of polyurethane, low density polyethylene, polypropylene, polybutylene, and silicone.

49. A wound dressing as defined in claim 3, wherein said flexible thin film layer and said flexible release backing layer both comprise a polyurethane film material.

50. A wound dressing as defined in claim 4, wherein said flexible thin film layer and said flexible release backing layer both comprise a polyurethane film material.

51. A wound dressing as defined in claim 4, wherein said release backing layer is divided into at least two backing pieces, a first of said backing pieces releasably attached to said adhesive layer on one side of a transverse axis of said flexible thin film layer and a second of said backing pieces releasably attached to said adhesive layer on another side of said transverse axis of said flexible thin film layer, each of said backing pieces having a pull-tab attached thereto, each said pull-tab extending away from said transverse axis of said flexible thin film layer.

52. A wound dressing as defined in claim 5, wherein said flexible thin film layer and said flexible release backing layer both comprise a polyurethane film material.

\* \* \* \* \*